United States Patent [19]
Eden et al.

[11] Patent Number: 5,411,893
[45] Date of Patent: May 2, 1995

[54] DRY SLIDE FOR DIAGNOSTIC TESTS

[75] Inventors: Ruth F. Eden; Jerry W. Smith, both of Ann Arbor; Amy T. Meszaros, Adrian; Leon F. Strenkoski, Dexter, all of Mich.

[73] Assignee: Difco Laboratories, Ann Arbor, Mich.

[21] Appl. No.: 31,660

[22] Filed: Mar. 15, 1993

[51] Int. Cl.⁶ .................... G01N 33/16; G01N 33/48
[52] U.S. Cl. .................... 436/165; 436/169; 436/808; 356/244; 422/56; 422/57; 422/58; 422/82.05; 422/86; 422/88; 435/4; 435/7.4; 435/805
[58] Field of Search .................... 422/56, 57, 58, 61, 422/73, 82.05, 82.08, 82.09, 86, 88; 436/69, 165, 121, 167, 110, 169, 106, 805, 808; 435/4, 7.1, 7.2, 7.4, 12, 13, 19, 21, 24, 27, 285, 288, 291, 808, 805; 356/244

[56] References Cited

U.S. PATENT DOCUMENTS

| | | | |
|---|---|---|---|
| 3,913,562 | 10/1975 | Moore et al. | 128/2 |
| 3,990,850 | 11/1976 | Friedman et al. | 23/230 |
| 3,996,006 | 12/1976 | Pagano | 23/253 |
| 4,225,557 | 9/1980 | Hartl et al. | 422/56 |
| 4,234,683 | 11/1980 | McMillan | 435/18 |
| 4,353,824 | 10/1982 | Schindler et al. | 260/156 |
| 4,472,353 | 9/1984 | Moore | 422/58 |
| 4,525,156 | 6/1985 | Benusa et al. | 604/28 |
| 4,565,783 | 1/1986 | Hansen et al. | 435/299 |
| 4,603,108 | 7/1986 | Bascomb | 435/34 |
| 4,668,472 | 5/1987 | Sakamoto et al. | 422/56 |
| 4,824,640 | 4/1989 | Hildebrand et al. | 422/56 |
| 4,960,691 | 10/1990 | Gordon et al. | 435/6 |
| 5,096,668 | 3/1992 | Thompson | 422/58 |

Primary Examiner—David A. Redding
Attorney, Agent, or Firm—Reising, Ethington, Barnard, Perry & Milton

[57] ABSTRACT

A test slide (10) for performing diagnostic tests for detecting the presence of cells, their enzymes, metabolites and other cellular derivatives. The test slide (10) comprises a support strip (14), a coating (34) comprising a carrier and a diagnostic reagent disposed on the support strip (14), and a mount (12) comprising a front wall (18) and a rear wall (20). The coating (34) has the properties of being dry and stable, and water soluble. Further, the coating (34) and the diagnostic reagent are capable of rehydration. The support strip (14) is disposed between the front wall (18) and the rear wall (20) of the mount (12). Both the front (18) and rear (20) walls can have coinciding openings (28,28a) that overlie the support strip (14) thereby allowing spectroscopic, visual and microscopic examination of the support strip (14).

34 Claims, 2 Drawing Sheets

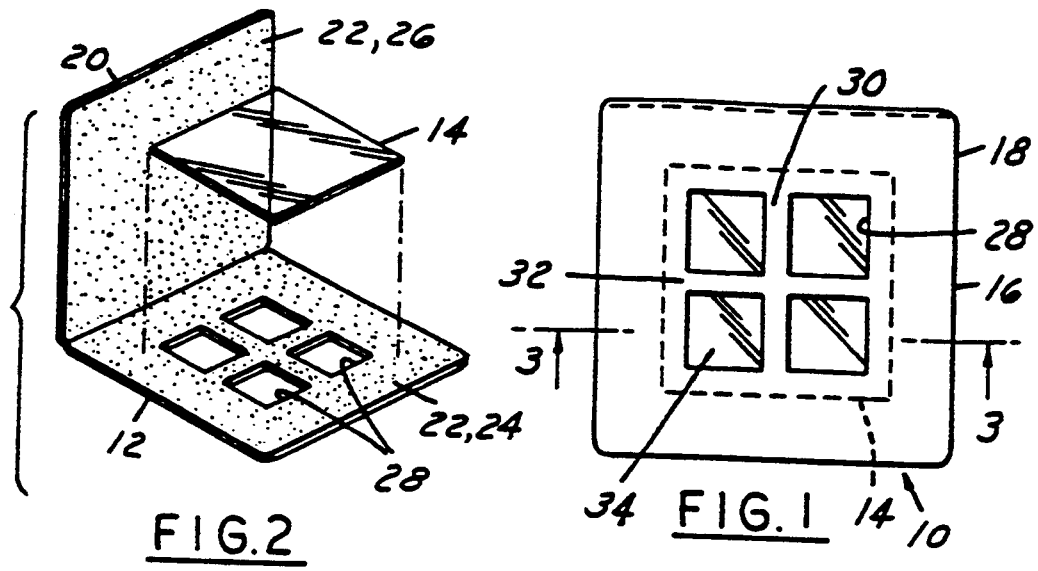
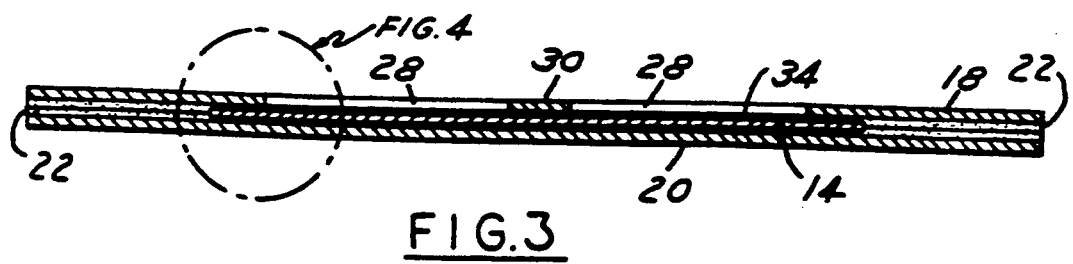
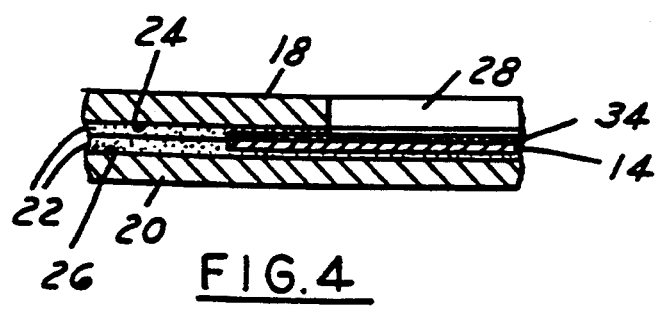

DRY SLIDE FOR DIAGNOSTIC TESTS

BACKGROUND OF THE INVENTION

TECHNICAL FIELD

This invention relates to a test slide for performing diagnostic tests.

BACKGROUND ART

Planar slides and cards are used to perform diagnostic tests, including blood, urine and sputum chemistry tests, as well as blood typing. Similar layered devices containing immobile nutrient components are used for culturing microorganisms. The cards and slides commonly contain a protective cover to protect and preserve the specimen or culture media during incubation or for storage purposes.

U.S. Pat. No. 3,990,850 describes a test card, which includes a substrate that has a test surface which is substantially insoluble in, impermeable to, non-absorbent to and wettable by water and carrying a dried test reagent. An end flap folds over the test area to enclose and preserve the specimen in a blood typing test. The card has a spot of blood typing anti-serum to which the blood sample is added. The flap has bonded thereon an absorbent blotting paper around the test area. The results may be viewed through a transparent plastic opening or window in the now folded flap.

U.S. Pat. No. 3,996,006 shows a test sheet which includes a sheet underlying openings in the front panel. Reagents are added to the paper sheet. The sheet may be divided into test sections. The '850 and '006 test slides are also described as useful for immunological tests.

The manufacture of these devices, if mentioned, is by spotting the test reagents in the reaction area and drying the test card. During manufacture, each card must be handled individually. For example, U.S. Pat. No. 4,668,472 generally describes manufacturing by forming cups or wells into which the reagents are dispensed. The forming, filling and drying operations can be performed on the same machine, with wells of the reagent prepared and cut out for assembly. Although this may streamline the manufacture, it limits the flexibility of manufacturing and leads to variability, that is, non-uniform reaction surface preparation.

U.S. Pat. No. 4,565,783 describes a device for culturing and observing microorganisms which may also be used for microbiological tests using antibiotics. A substrate is coated with an adhesive and a water soluble powder, which includes a nutrient or gel, which is adhered to the adhesive. A cover sheet protects the culture and microorganism from contamination during incubation and growth. The device also includes an opening with limits for retaining fluid. This device is useful where incubation is required and where liquids are added. The device requires a cover sheet to isolate the contents from the environment, prevent evaporation and to prevent contact by the user during incubation and handling. Thus the prior art has provided test cards and slides for culturing microorganisms and for wet specimen analysis.

However, the above test cards are expensive to manufacture and are not adaptable to multiple or combinations of tests simultaneously on the same sample.

U.S. Pat. No. 5,096,668 to Thompson issued Mar. 17, 1992 and assigned to the assignee of the subject invention, while not prior art, does provide an inexpensive production method of preparing test cards. This invention is a diagnostic test slide for performing diagnostic tests for detecting the presence of microorganisms, enzymes or metabolites comprising a plastic film having a coating therein comprising a carrier and a reagent. The coated film is placed in a mount that is constructed and arranged to form a border around a portion of the film. A method is provided for making the test slide utilizing conventional, automated devices for making coated photographic films, and conventional, automated devices for mounting slide film in mounts. However, this test slide does not allow for the microscopic visualization of the microorganisms and their reaction to diagnostic reagents.

SUMMARY OF THE INVENTION AND ADVANTAGES

The present invention is a test slide for performing diagnostic tests for detecting the presence of cells, their enzymes, metabolites and other cellular derivatives. The test slide includes a support strip that is dimensionally stable and has a top surface and a bottom surface. The test slide further includes a coating bonding directly to the top surface of the support strip. The coating comprises a carrier and a diagnostic reagent and has the properties of being dry and stable, and water soluble. Further, the coating is capable of rehydration. The test slide further includes a mount comprising a front wall and a rear wall. The support strip is disposed between the front wall and the rear wall of the mount. Both the front and rear walls can have coinciding openings that overlie the support strip thereby allowing spectroscopic, visual and microscopic examination of the support strip.

The present invention provides an improvement on the test slide described in the '668 patent in that microscopic examination of the support strip is now available. Further, the present invention has the advantage that it provides a test slide for performing diagnostic tests on cells; additionally the test slide is constructed so as to not require assembly after the analysis is initiated. The test reagent carried on the slide is in a dry format, ready for use. Further, the test reagent is conveniently included in a dry carrier without the need for adhesive to bind the carrier to the test slide and is easily handled so that the test slide is more economical and easier to manufacture than prior art slides and cards.

The invention has the advantage of proving a process that allows automated or semi-automated assembly of the test slides which is labor saving, economical, and which eliminates variability of reactions by preparing the reaction surface in a uniform manner.

BRIEF DESCRIPTION OF THE DRAWINGS

Other advantages of the present invention will be readily appreciated as the same becomes better understood by reference to the following detailed description when considered in connection with the accompanying drawings wherein:

FIG. 1 is a top view of the test slide embodying the invention;

FIG. 2 is an exploded view of the elements of the slide of FIG. 1 of an alternative embodiment, prior to assembly;

FIG. 3 is a sectional view taken along line 3—3 of FIG. 1;

FIG. 4 is an enlarged sectional view taken at the encircled portion of FIG. 3;

DETAILED DESCRIPTION OF THE PREFERRED EMBODIMENT

Figure 5:
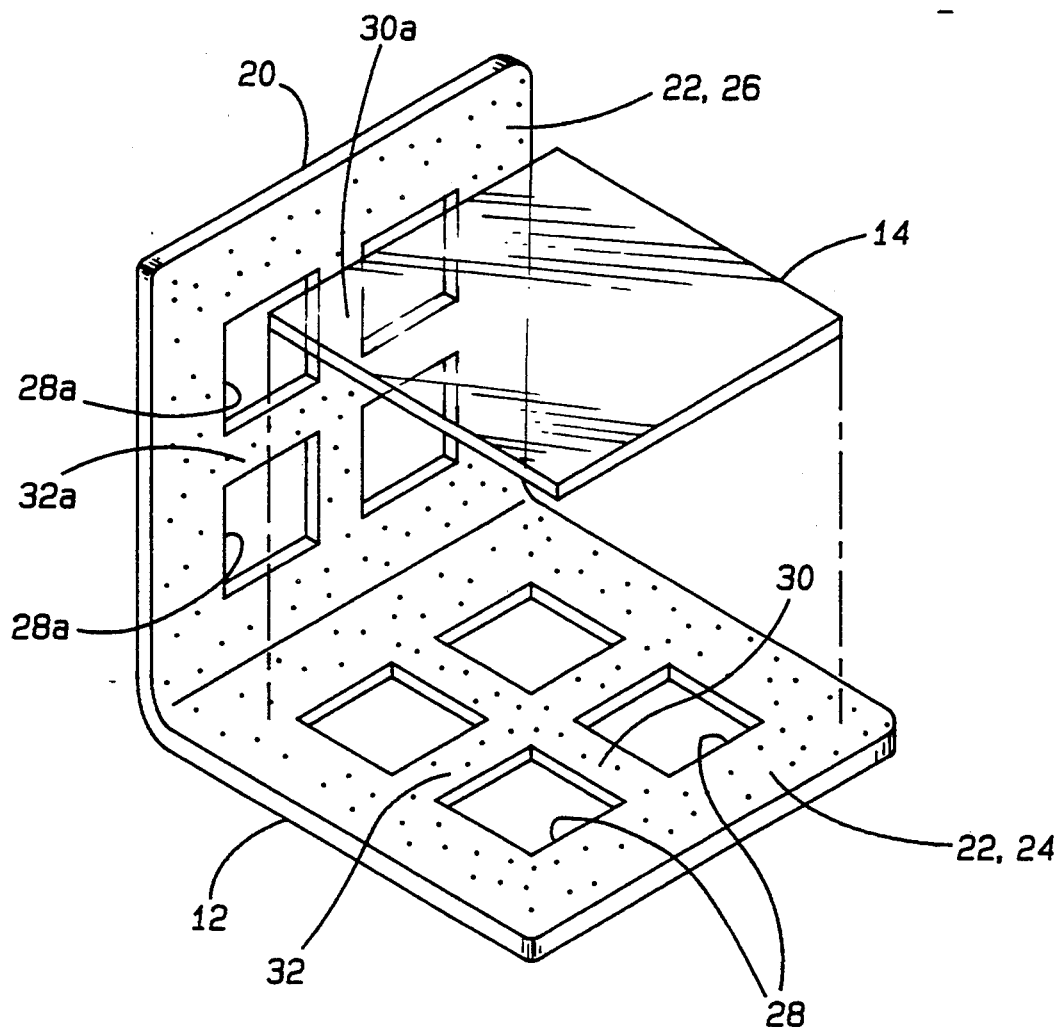
FIG. 5 is an exploded view of the elements of the test slide of FIG. 1 of the instant invention prior to assembly.

Referring to FIGS. 1 and 5, there is shown a test slide 10 which embodies the invention. The slide 10 basically comprises a mount 12 and a support strip 14. The mount 12 is constructed and arranged to form a border 16 around the support strip 14. The support strip 14 is stabilized and secured by the mount 12. The mount 12 has a front wall 18 and a rear wall 20. Preferably, the mount 12 is of a semi-rigid plastic or cardboard material.

The front wall 18 has at least one opening 28 to provide access to the support strip 14. Preferably, there are four spaced openings 28, formed in the wall 18 by cross pieces 30, 32 of the wall 18. In a preferred embodiment the rear wall 20 also has at least one coinciding opening 28a to provide viewing access to the support strip 14. That is, the openings 28,28a in the front 18 and rear 20 wall can be superimposed or correspond such that an opening through the entire mount 12 is formed. Preferably, as in the front wall 18, there are four spaced openings 28a, formed in the rear wall 20 by crosspieces 30a,32a of the rear wall 28a.

In an alternative embodiment, not all of the spaced openings 28 in the front wall 18 have corresponding or coincidental openings 28a formed in the rear wall 20. This configuration makes possible certain combinations of diagnostic tests as discussed below. In still further embodiments the spaced openings 28 in the front wall 18 do not have coincidental openings 28a formed in the rear wall 20, in other words the rear wall is solid.

The front 18 and rear 20 walls have interior surfaces 26,28 respectively that are facing each other. The support strip 14 is disposed between the front 18 and rear 20 walls; in other words, it is sandwiched between them with the interior surfaces 26,28 adjacent the support strip 14.

In one embodiment an outer margin of the support strip 14 is attached to the mount 12 by a pressure sensitive adhesive 22 disposed on either or both opposing internal surfaces (24,26) at least in an area surrounding the openings (28,28a) as best shown in FIG. 4. To finalize assembly of the mount 12, the adhesive 22 can cover the entire opposing internal surfaces 24,26 such that the internal surfaces 24,26 will be bound to one another when the two walls are fitted together. The front 18 and rear 20 walls are securely fastened to each other in this way. Alternatively, the finalization of the assembly can utilize a clasp (not shown) to hold the opposing internal surfaces 24,26 contiguous to each other with the support strip 14 adhesively attached to one of the internal surfaces 24,26. The front 18 and rear 20 walls are thereby securely fastened, with the ability to reopen the mount 12.

In an alternative embodiment, the clasp holds the opposing internal surfaces 24,26 contiguous with the support strip 14 sandwiched between them without an adhesive. The mount 12 can therefore be reopened if needed.

After assembly, cells or cellular enzymes, metabolites and other derivatives can be placed on the coating. 34 on the support strip 14, preferably through the opening 28 in the front wall 18 adjacent to the top surface of the support strip 14. Any spectroscopic or visible changes which occur indicating the diagnostic reagent has changed in response to the application can be observed through the opening 28 in the front wall 18. If needed for microscopic visualization a cover slip (not shown) can be added after the reaction is completed.

As shown in FIGS. 3 and 4, a coating 34 is bonded to the top surface of the support strip 14 or impregnated into the support strip 14 before it is enclosed by the mount 12. The coating 34 comprises a carrier and a diagnostic reagent. The coating 34 is dry and stable. Preferably, the coating remains stable and sticky when wetted. The coating 34 desirably has a coating weight of less than 2 mg (milligrams) per square inch and preferably 1 mg per square inch.

The carrier can be selected from among, but not limited to, the group consisting of gelatin, polygalacturonic acid, pectin, agar, agarose, cellulose, carboxymethyl cellulose, guar, xanthan, acacia, similar plant gums, starch, polyvinyl alcohol, polyvinyl chloride and polyacrylamide depending on the diagnostic reagent being utilized and the type of support strip 14.

In selecting the carrier care is taken not to use carriers which can be metabolized by the cells being placed on the test slide or which can react with the diagnostic reagent nonspecifically, as are well known to those in the art. The carrier is selected to be an inactive ingredient vis-à-vis the cells being tested or the diagnostic reagent being utilized. Such reactions are well known to those in the art.

The support strip 14 can be formed from glass, plastic materials and paper materials. In one preferred embodiment, the support strip 14 is in the form of a plastic film. Desirably, the strip of film 14 is less than 1/64 or 0.015 of an inch thick and is preferably 0.005 of an inch thick. The plastic material can be selected from among, but not limited to, polyethylene, polyester, polyvinyl chloride (PVC), polyethylene terephthalate (PET), polyethylene terephthalate glycol (PETG), cellulose triacetate, and polycarbonate. When paper material is utilized in forming the support strip 14 it can be selected from among, but not limited to, absorbent paper, plastic-backed paper, membrane covered absorbent paper, and porous membrane covered absorbent paper. The specific selection is determined in connection with the carrier and diagnostic reagent according to selection parameters known to those skilled in the art.

Advantageously, the test slide 10 may be manufactured in a relatively economical continuous processes. When the support strip 14 is of a material which is flexible and dimensionally stable, the support strip 14 can be handled as roll stock; if not flexible as sheet stock. The coating 34 can be applied to large rolls and cut down to final size, thereby lowering coating costs. The support strip 14, once coated either continuously or by spot dispensing, can also be rolled and handled as roll stock. The support strip 14 and mount 12 can be handled by commercially available, inexpensive, photographic slide mounting machines, allowing automated assembly of the slide 10 Commercial machines can also print alpha-numerical data onto the mount 12, lowering production costs further. Finally, the support strip 14 can be coated by conventional coating equipment. Importantly, existing standard technology for the coating industry, paper impregnation industry, spot dispensing industry, and the film making industry can be utilized.

For example, support strips 14 can be formed from sheet or roll stock of plastic. The coating 34 may be applied to the sheet or roll stock and, after it has dried, the strips may be formed by cutting the coated sheet or roll stock to the desired size. It has been found that sheet or roll stock is available, having a width in the range of 2" to 48". Coated strips have been produced from the stock which are approximately 35 mm wide. The stock may be cut using rotary knives in an automated process.

The support strips 14 of the invention are not required to be perforated whereas conventional 35 mm photographic film is often perforated. Therefore, it may be necessary to modify the conventional slide mounting device to adapt to roll stock, which is not perforated. For example, the sprockets on the rollers or wheels of a conventional slide mounting device may need to be replaced.

Advantageously, conventional film coating devices can be used to coat roll stock. For example, devices for coating an emulsion onto a photographic film, are well known and available. The conventional film coating devices are automated devices which coat, dry and roll up the coated film in a continuous process. The coating may be applied by means of extrusion, dipping, spraying, spot dispensing or other existing methods of coating. The coating may also be applied using a wire wound draw down bar where the wire diameter is in the range of about 0.006 to 0.018 inches in diameter.

Diagnostic reagents can be selected from among, but not limited to, those for detecting: oxidase, beta lactamase, L-aniline amino peptidase (Gram reaction), indole, catalase, coagulase, urease, $H_2S$, Voges-Proskauer, bile esculin, phosphatase, B-glucosidase, citrate utilization, nitrate, $C_8$ Esterase activity, pyrrolidonyl aminopeptidase (PYR), glucuronidase activity, antibodies, antigen-antibody reactions, latex tests, cellular staining, antibiotic sensitivity, high level aminoglycoside resistance, other cellular metabolites and enzymes, drug sensitivity, toxins and other types of agglutination assays. As for example, test slides 10 can be prepared to detect cytochrome c oxidase, beta lactamase and L-alanine amino peptidase (a Gram stain replacement test). In the cytochrome c oxidase test, a positive reaction may be indicated by a color change of organic electron acceptors or donors. In this test, the diagnostic reagent may incorporate ascorbic acid and tetramethyl phenylene diamine dihydrochloride.

In the beta lactamase test, the active part of a beta lactam antibiotic is a beta lactam ring which has a defined chemical composition. Organisms which possess beta-lactamases, may be resistant to the antibiotic by breaking open the ring. The beta lactamase test is a test for the presence of enzymes that cleave the beta lactam ring. For example, Penicillin G and chromogenic cephalosporins may be used as the active component of the reagent layer.

The L-alanine amino peptidase test is a test which correlates well with the well known Gram stain technique in microbiology. If the chromogenic substrate is cleaved, the organism is a Gram negative strain. If the substrate is not cleaved, the organism is a Gram positive strain.

Examples of additional tests that can be performed in this format include: Phosphatase using indoxyl or bromo-chloro-indoxyl phosphate, glucuronidase, urease, ortho-nitrophenyl galactosidase, acid from sugar fermentation, pyrrolidoxyl aminopeptidase, esterase, N-acetyl-B,D-galactosamidase, protease and hydrogen sulfide production are examples of assays that can be performed in this format. Fluorogenic substrates can be incorporated into the film as the bioactive reagent. 4-Methylumbelliferyl glucuronide is an example. Organisms that produce glucuronidase, such as *Escherichia coli*, will cleave the reagent, producing methylumbelliferone. This reaction can be monitored by shining an ultraviolet lamp on the film. A blue fluorescence will indicate a positive reaction. No fluorescence will be indicative of a negative reaction.

Agglutination tests, whether direct or indirect, as well as hemagglutination inhibition and the Coombs Test, can be performed with the preferred embodiment of the test slide 10 as shown in FIG. 5 since microscopic evaluation of cellular or particle clumping is possible. As an example of this, latex agglutination (fixation) is described in the examples.

A combination of tests is possible by utilizing a plurality of diagnostic reagents in combination, as long as the combined reagents do not mask each other or otherwise interact with each other to interfere with a response. In a first embodiment the various diagnostic reagents are combined with the carrier to form the coating. In this embodiment a plurality of colorimetric and fluorimetric tests can be combined. For example, one colorimetric and one fluorimetric test could be combined or a simple combination of two fluorimetric or colorimetric tests are possible. For fluorimetric tests, the fluorimetric reagents would need to emit at different wavelengths and not mask each other as are known to those skilled in the art. For colorimetric tests similar constraints must be considered as are known to those skilled in the art.

In a second embodiment, different diagnostic reagents can be spotted in different openings 28 in the test slide 10 using spot dispensing technology. Generally, the test slide 10 is assembled prior to the spot dispensing. Depending on the nature of the diagnostic test the opening 28 may or may not have a coinciding opening 28a in the back wall 20. For example for diagnostic staining tests requiring microscopic evaluation there will be a coinciding opening 28a for at least the opening wherein the diagnostic staining test is performed.

It is possible to prepare a kit with modifying and indicating means for identifying cell types or cellular enzymes, metabolites, and other derivative of interest, which includes reagents, standards and instructions. Modifying means are provided for selecting specific cell types from a sample or for inducing production of cellular enzymes, metabolites or other cellular derivatives of interest. Specific selective agents that will only allow certain cell types to grow can be provided. Inductive agents which will either stimulate specific cells or induce specific cells to make a specific product can also be provided. After incubation with the modifying agent or agents, the indicating means for the cell type or cellular derivative is undertaken. The appropriate test slide (10) as described above is used as the indicator means. An example of such a kit is given in Examples 12 and 13.

The presence of any cells or cellular enzyme, metabolite, and other derivative of interest in diagnostics can be monitored, providing either spectrographic, visual or microscopic changes occur.

EXAMPLE 1

METHOD OF MAKING A CYTOCHROME C OXIDASE TEST SLIDE:

(1) A cellulose triacetate film of 5 thousandths of an inch thickness was used.

(2) A gelatin/reagent mixture was prepared which included:
 (a) Bacto ® gelatin (Difco Laboratories, Detroit, Mich.) 12% wt/volume 10 mls;
 (b) Ascorbic acid solution 0.1% 1.1 mls;
 (c) NNN'N' tetramethyl-1, 4-phenylene diamine dihydrochloride 0.1 g in distilled or deionized water.

(3) The gelatin solution was melted, cooled to approximately 35° C., and the reactive components were added.

(4) The gelatin/reagent mixture was applied to the film at about 35° C. using a #12 draw down bar yielding a coating weight of approximately 1 mg/sq. inch (dry).

(5) The coated film was dried in air overnight.

(6) The film was cut into pieces approximately 35 mm by 37 mm.

(7) The film was mounted in plastic or paper slide mounts.

EXAMPLE 2

METHOD OF PERFORMING OXIDASE TEST

The user rubbed 1 to 4 colonies of microorganisms onto the reagent on the slide, prepared according to the method of Example 1, through an aperture. The Oxidase positive organism such as *Pseudomonas aeruginosa* rehydrated and metabolized the substrates resulting in a reaction that produced a color change to purple or dark purple within 20 seconds. An organism negative for the test, such as *Escherichia coli*, will be unable to oxidize the substrate and no color change will result. The user read the positive or negative result through the aperture of the test card.

There are other reagents which may be used to make the test slide. For the oxidase test, the reagents include other reducing agents, such as thioglycollate, sodium sulfide, mercaptoethanol, dithiothreitol, dithioerythritol, and other oxidase substrates, such as p-aminodiethylaniline oxalate.

EXAMPLE 3

METHOD OF MAKING A BETA-LACTAMASE TEST SLIDE (1) A absorbent paper was used.

(2) A reagent mixture was prepared which included either:
 I (a) 1 mM sodium citrate;
 (b) Chlorophenol red solution, 0.085%;
 (c) methyl alcohol, 40%;
 (d) Penicillin G. potassium salt, 5%;
 (e) and the reagent mixture was adjusted to pH 8.5 with 1N sodium hydroxide. or
 II 0.05% chromogenic cephalosporin in methyl alcohol.

(3) The absorbent paper was impregnated with either reagent I or II.

(4) The paper was dried using forced air at about 20° C.

(5) The paper was cut into pieces approximately 35 mm by 38 mm.

(6) The paper was mounted in plastic or paper slide mounts.

EXAMPLE 4

METHOD OF PERFORMING BETA-LACTAMASE TEST

Utilizing the test slide prepared according to the method of Example 3, the user rehydrated the reagent with a small drop of water and rubbed 1–2 colonies of microorganisms onto the moistened reaction area. A color change resulted, based on the cleavage of the beta-lactam ring and net acidification of the reagent mixture or of the formation of a chromogen, in the case of the chromogenic cephalosporin substrates for beta-lactamese positive strains, such as *Hemophilus influenzae* ATCC 35056. Beta-lactamase negative strains, such as *Hemophilus influenzae* ATCC 8149 developed no color change within the 30 minute test duration.

For the beta-lactamase test, the reagents may include other antibiotics, such as penicillin V, nitrocefin and related compounds (Glaxo), cephalothin, and other cephalosporins, PADAC (Pyridinum 2-AZO-p-dimethylaniline chromophore [Hoechst-Roussell]) and chromogenic cephalosporins as cited in U.S. Pat. Nos. 4,525,156 and 4,353,824 and the like. Other buffers include citrate, Hepes, tris, maleate, barbitone, and the like. Other pH indicators include phenol red, brom thymol blue, brom cresol purple and the like.

EXAMPLE 5

METHOD OF MAKING A L-ALANINE AMINO PEPTIDASE TEST SLIDE (1) A cellulose triacetate film about 5 thousandths of an inch thickness was used.

(2) A gelatin/reagent mixture was prepared which included:
 (a) Bacto ® gelatin 12% wt/vol, 10 mls;
 (b) L-alanine nitro anilide, at approximately 0.5% in the gelatin solution.

(3) The gelatin/reagent mixture was applied to the film at about 35° C. yielding a coating weight of approximately 1 mg/sq. inch (dry).

(4) The coated film was dried using forced air at about 30° C.

(5) The film was cut into pieces approximately 35 mm by 37 mm.

(6) The film was mounted in plastic or paper slide mounts.

EXAMPLE 6

METHOD OF MAKING A LATEX TEST SLIDE (1) A cellulose triacetate film about 5 thousandths of an inch thickness was used.

(2) A PVA/latex mixture was prepared which included:
 (a) Latex particles bound to antibodies for pathogens such as Listeria, Staphylococcus, Streptococcus, and the like;
 (b) 10% PVA in water or buffer solution (as a plasticizer and stabilizing agent); and
 (c) 0.05% Nonidet P-40 Solution (for ease of rehydration).

(3) The PVA/latex mixture was applied to the film by spot dispensing approximately 10 µl per testing spot.

(4) The film was dried using forced air approximately 56° C.

(5) The film was cut into pieces approximately 35 mm×38 mm.

(6) The film was mounted in plastic or paper slide mounts of the variety that display four round windows and a closed back.

EXAMPLE 7

METHOD OF USING A LATEX TEST SLIDE

Using the slide prepared according to the method of Example 6, the user made a suspension of the test culture and dispensed approximately 30 μl onto a dried latex test spot on the film, or the user dispensed approximately 30 μl water onto the film and mixed a loopful of culture into the drop. The test culture was mixed into the latex to rehydrate it. The slide was rotated in either a circular or rocking motion for one minute. An organisms negative for the Listeria test, such as *H. influenzae* ATCC 10211, remained turbid. An organism positive for the Listeria test, such as *L. monocytogenes* ATCC 19111, agglutinated the latex forming visible clumps within the time limits of the test.

EXAMPLE 8

METHOD OF MAKING A COAGULASE TEST SLIDE (1) A cellulose tri-acetate film about 5 thousandths of an inch was used.

(2) A PVA/rabbit plasma mixture was prepared as follows:
  (a) PVA (poly vinyl alcohol) solution, 10% wt/vol was prepared.
  (b) Aniline Blue, at approximately 2% in the PVA solution.
  (c) This PVA/Aniline Blue Solution was used to reconstitute lyophilized rabbit plasma.

(3) The PVA/rabbit plasma mixture was applied to the film using a draw down bar in the range of #18–#30, or by using other known coating methods that exist in the coating industry.

(4) The coated film was dried at a temperature range of 30° C.–58° C.

(5) The film was cut into pieces approximately 35 mm×38 mm.

(6) The film was mounted in plastic or paper slide mounts.

EXAMPLE 9

METHOD OF USING A COAGULASE SLIDE TEST

The user rubbed 2–6 colonies of microorganisms onto the coating on the film prepared according to the method of Example 8. One drop of water was added to the microorganisms. The colonies were mixed into the water with a stirring motion. Coagulase positive organisms, such as *S. aureus* 25923, caused the rabbit plasma to agglutinate and form clumps on the film. The aniline blue served to stain the clumps blue and make them easier to see. Coagulase negative organisms, such as *Staph epidermidis* CDC 5-59, did not cause the rabbit plasma to agglutinate and the drop was turbid from the distribution of the organism. The aniline blue served to stain the organism/water mixture and provide a contrast to the white background of the mount.

This device allowed the user to differentiate between *S. aureus* and other Staphylococcus species.

EXAMPLE 10

METHOD OF MAKING A STAINING TEST SLIDE (1) A cellulose triacetate film of 5 thousandths of an inch thickness was used.

(2) A PVA/stain mixture was prepared by mixing:
  (a) Poly vinyl alcohol 10% wt/vol;
  (b) Acridine Orange (0.1% in buffer), or Methylene Blue (5% in ethanol), or Safranin (1% in ethanol), or Crystal Violet (3% in ethanol), or Brilliant Green (5% in ethanol), or Basic Fuschia (5% in ethanol), or Methyl Red (5% in ethanol), or Aniline Blue (2% in water).

(3) The PVA/dye mixtures were applied to the film using a #6 draw down bar.

(4) The film was dried between 22° C. and 58° F. using forced air.

(5) The film was cut into pieces approximately 35 mm×38 mm.

(6) The film was mounted in plastic or paper slide mounts of the variety that display an open front and an open back.

EXAMPLE 11

METHOD OF USING A STAINING TEST SLIDE

The user moistened the test slide prepared according to the method of Example 10 with a small amount of water and suspended 1–5 colonies of microorganisms in the drop with a stirring motion. The slide was allowed to air dry (approximately 10 minutes) or the drop was covered with a cover slip The slide was placed on a microscope stage and viewed for colony appearance with and without immersion oil. Representative microorganisms from both cocci, such as *S. aureus* ATCC 25923, and rod, such as *E. coli* ATCC 25922, groups were tested. The colony morphology was apparent as the microorganisms were stained by the dyes.

EXAMPLE 12

METHOD OF MAKING A HIGH LEVEL AMINOGLYCOSIDE RESISTANCE (HLAR) SCREEN TEST KIT (1) Impregnate filter paper with a high level aminoglycoside and growth medium.

(2) Impregnate filter paper web with a reagent mixture:
  (a) 1% Dextrose or other carbon source and a pH indicator; or
  (b) Redox indicator; or
  (c) Other indicator of organism viability.

(3) Dry paper from Steps 1 and 2 using forced air heated to approximately 30° C.

(4) Cut paper from Step 1 in ¼" disks.

(5) Cut paper from Step 2 into approximately 35 mm×38 mm pieces.

(6) Mount the paper from Step 5 in plastic or paper slide mounts.

EXAMPLE 13

METHOD OF USING A HLAR TEST KIT

The user dispensed one ¼" disk into a small test tube and rehydrated with a small volume, approximately 250 μl, sterile water which allowed the high level aminoglycoside and growth medium to leach into the water. The user added enough of the test culture microorganisms to achieve a standard number of organisms in the test tube. The user incubated the test tube at 37° C. for 1-3 hours. Organisms which were resistant to the aminoglycoside in the test tube survived the incubation step and remained viable. Organisms which were sensitive to the aminoglycoside were killed during the incubation step and were no longer viable. The user dispensed a drop of the test culture onto the paper mounted in the test slide as prepared according to the method in Example 12. Viable organisms either reduced the redox indicator or utilized the carbon source and formed an acidic environment, thus changing the pH indicator. In either case, a color reaction occurred upon reduction of a redox indicator or by the acid shift of the pH indicator. The color change was evidence of viability of the test culture. Therefore, a color change is evidence of aminoglycoside resistance by the test culture.

EXAMPLE 14

METHOD OF MAKING A COMBINATION TEST SLIDE (1) Impregnate filter paper with a combination of substrates, such as
  (a) 1% Alanine-7-amido-4-methylcoumarin Trifluoroacetate Salt (AAMC); and
  (b) 0.5% 5-Bromo-4-chloro-3-indolyl-$\beta$-D-glycuronic acid (BCI-glucuronic acid) in
  (c) Tris Buffer.

(2) The paper was dried using forced air heat at approximately 30° C.

(3) The impregnated paper was cut into pieces approximately 35 mm×38 mm.

(4) The paper was mounted in plastic or paper slide mounts.

EXAMPLE 15

METHOD OF USING A COMBINATION TEST SLIDE FOR DETECTING THE GRAM REACTION AND GLUCURONIDASE REACTION OF BACTERIA

The user rehydrated a reaction area of the slide prepared according to the method of Example 14 with a small drop of water. Four to six colonies of microorganisms were smeared onto the moistened reaction area.

Reaction 1: The user shone an UV lamp (Wood's Lamp) onto the slide. The amino peptidase found in Gram negative organisms (such as *E. coli* ATCC 25422) cleaved the AAMC resulting in a blue fluorescence. If the test organism was Gram positive (such as *S. aureus* ATCC 25923), the reaction area did not fluoresce. The user observed for fluorescence within one minute to indicate that the test organism was of the Gram negative or Gram positive classification.

Reaction 2: The user placed the slide in an incubator at 37° C. for 15-30 minutes. The user observed the slide for a blue/green color. Glucuronidase positive organisms (such as *E. coli* ATCC 25922) cleaved the BCI-glucuronic acid producing a blue/green precipitate. Microorganisms negative for glucuronidase (such as *Klebsiella pneumoniae* ATCC 13883) did not cleave the substrate and remain colorless.

Therefore, the combination test slide allowed the user to take an unknown culture and determine both its Gram reaction and presence/absence of glucuronidase activity. This was useful in the differentiation of *E. coli* organisms, which are known to be Gram negative and glucuronidase positive, from other microorganisms, such as *Klebsiella pneumoniae*, which are Gram negative, but glucuronidase negative.

It can thus be seen that in these examples, cells, enzymes, metabolites or cellular derivatives are added onto a slide coated with a reagent and a change in the diagnostic reagent can be monitored by spectrographic, visual, and microscopic means. The tests are conveniently done with the diagnostic slide which does not require assembly after the analysis is done; which has at least one test reagent on the slide; which can have a coinciding opening on the rear wall to facilitate microscopic examination and which is easy to handle.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims wherein reference numerals are merely for convenience and are not to be in any way limiting, the invention may be practiced otherwise than as specifically described.

What is claimed is:

1. A test slide for performing diagnostic tests for detecting the presence of cells, their enzymes, metabolites and other cellular derivatives, said test slide comprising:
   a support strip being dimensionally stable and having a top surface and a bottom surface,
   a coating directly adhering to said support strip,
   said coating comprising a carrier and a diagnostic reagent,
   said coating being dry and stable, and water soluble,
   said coating and said reagent being capable of rehydration,
   a mount comprising a front wall and a rear wall,
   said support strip being disposed between said front wall and said rear wall, and
   wherein said front and rear walls having at least one coinciding opening that overlie said support strip thereby allowing spectroscopic, visual and microscopic examination of said support strip.

2. The test slide of claim 1 wherein the front and rear walls have four coinciding openings.

3. The test slide of claim 2 further comprising at least one of said openings formed in said front wall without said coinciding opening in said rear wall.

4. The test slide of claim 1 wherein said coating comprises a plurality of diagnostic reagents.

5. The test slide of claim 1 further comprising said support strip being composed of glass, plastic material or paper material.

6. The test slide of claim 5 further comprising by said support strip being in the form of a plastic film.

7. The support strip of claim 5 wherein said plastic material is selected from the group consisting of polyethylene, polyester, polyvinyl chloride, polyethylene terephthalate, polyethylene terephthalate glycol, cellulose triacetate, and polycarbonate.

8. The support strip of claim 5 wherein said paper material is selected from the group consisting of absorbent paper, plastic-backed paper, membrane covered absorbent paper, and porous membrane covered absorbent paper.

9. The test slide of claim 1 further comprising said coating covering said entire top surface.

10. The test slide of claim 1 wherein said carrier is selected from the group consisting of gelatin, polygalacturonic acid, pectin, agar, agarose, cellulose, carboxymethyl cellulose, guar, xanthan, acacia, plant gums, starch, polyvinyl alcohol, polyvinyl chloride and polyacrylamide.

11. The test slide of claim 1 wherein said front and rear walls include opposing internal surfaces, further comprising by an outer margin of said support strip attached to said mount by an adhesive disposed on either or both opposing internal surfaces at least in an area surrounding said openings.

12. The test slide of claim 11 further comprising said adhesive covering said opposing internal surfaces such that said internal surfaces are bound to one another and thereby said front and rear walls are securely fastened to each other.

13. The test slide of claim 11 further comprising a clasp holding said opposing internal surfaces contiguous such that said front and rear walls are securely fastened with the ability to open said mount.

14. The test slide of claim 1 wherein said front and rear walls include opposing internal surfaces, further comprising a clasp holding said opposing internal surfaces contiguous with said support strip sandwiched between such that said front and rear walls are securely fastened.

15. The test slide of claim 1 wherein said mount is of a semi-rigid material selected from the group consisting of plastic material and cardboard material.

16. A method of making a test slide for performing diagnostic tests for detecting the presence of cells, their enzymes, metabolites and other cellular derivatives, said method comprising:
 forming a support strip being dimensionally stable and having a top surface and a bottom surface,
 preparing a coating comprising a carrier and a diagnostic reagent being dry and stable, water soluble, and capable of rehydration,
 bonding the coating by its own properties to the support strip,
 mounting the support strip in a mount comprising a front wall and a rear wall, the support strip being disposed between the front wall and the rear wall, and
 placing at least one coinciding openings in the front wall and the rear wall that overlie the support strip such that spectroscopic, visual and microscopic examination of changes in the diagnostic reagent disposed on the support strip can be monitored.

17. The method of claim 16 wherein said step of preparing the coating includes a plurality of diagnostic reagents.

18. The method of claim 16 further comprising forming the support strip of glass, plastic material or paper material.

19. The method of claim 18 wherein said step of forming the support strip is in the form of a plastic film.

20. The method of claim 18 further comprising selecting the plastic material from the group consisting of polyethylene, polyester, polyvinyl chloride, polyethylene terephthalate, polyethylene terephthalate glycol, cellulose triacetate, and polycarbonate.

21. The method of claim 18 further comprising selecting paper material from the group consisting of absorbent paper, plastic-backed paper, membrane covered absorbent paper, and porous membrane covered absorbent paper.

22. The method of claim 6 wherein said step of bonding the coating includes applying the coating to the entire top surface.

23. The method of claim 17 further comprising selecting the carrier from the group consisting of gelatin, polygalacturonic acid, pectin, agar, agarose, cellulose, carboxymethyl cellulose, guar, xanthan, acacia, plant gums, starch, polyvinyl alcohol, polyvinyl chloride and polyacrylamide.

24. The method of claim 16 further comprising forming four coinciding openings in each of the front and rear walls of the mount.

25. The method of claim 24 further comprising forming at least one of said openings in said front wall without said coinciding opening in said rear wall.

26. The method of claim 16 wherein said step of mounting the support strip includes forming front and rear walls having opposing internal surfaces, and an outer margin of the support strip attached to the mount by an adhesive disposed on either or both opposing internal surfaces at least in an area surrounding the openings.

27. The method of claim 26 further comprising covering the opposing internal surfaces with the adhesive such that the internal surfaces are bound to one another and thereby said front and rear walls are securely fastened to each other.

28. The method of claim 26 further comprising holding the opposing internal surfaces contiguous such that said front and rear walls are securely fastened by a clasp.

29. The method of claim 16 further comprising forming front and rear walls having opposing internal surfaces and holding the opposing internal surfaces contiguous with said support strip sandwiched between such that said front and rear walls are securely fastened by a clasp.

30. The method of claim 16 further comprising forming the mount from a semi-rigid material selected from the group consisting of plastic material and cardboard material.

31. A method of detecting the presence of cells: their enzymes, metabolites and other cellular derivatives comprising:
 providing the test slide of claim 1, using the test applying a cell, its enzymes, metabolites or other cellular derivatives on the coating on the support strip through the opening adjacent the top surface of the support strip through the opening, and
 observing any spectroscopic, visible or microscopic changes which occur indicating the diagnostic reagent has changed in response to the application.

32. A test slide as set forth in claim 1 wherein said coating impregnates said support strip.

33. A method as set forth in claim 16 wherein said step of bonding the coating incudes spot dispensing the coating onto the top surface.

34. A method as set forth in claim 16 wherein said step of bonding the coating includes impregnating the support strip with the coating.

* * * * *